US006699670B2

(12) United States Patent
Rothman et al.

(10) Patent No.: US 6,699,670 B2
(45) Date of Patent: Mar. 2, 2004

(54) QUANTITATIVE ASSAY FOR THE SIMULTANEOUS DETECTION AND SPECIATION OF BACTERIAL INFECTIONS

(75) Inventors: Richard Eric Rothman, Cockeysville, MD (US); Samuel Yang, Baltimore, MD (US); Shin Lin, Baltimore, MD (US); Gabor David Kelen, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/085,134

(22) Filed: Mar. 1, 2002

(65) Prior Publication Data

US 2003/0124545 A1 Jul. 3, 2003

Related U.S. Application Data

(60) Provisional application No. 60/272,642, filed on Mar. 1, 2001.

(51) Int. Cl.[7] .......................... C12Q 1/68; C12P 19/34; C07H 21/02; C07H 21/04; C07H 21/00

(52) U.S. Cl. ......................... 435/6; 435/91.1; 435/91.2; 435/91.21; 536/24.3; 536/24.32; 536/24.33; 536/25.32

(58) Field of Search ........................... 536/24.33, 24.32, 536/24.3, 25.32, 26.6; 435/6, 810, 91.1, 91.2, 91.21

(56) References Cited

U.S. PATENT DOCUMENTS

| | | | | |
|---|---|---|---|---|
| 5,401,631 | A | 3/1995 | Lane et al. | |
| 5,851,767 | A | * 12/1998 | Stanbridge et al. | 435/6 |
| 6,235,504 | B1 | 5/2001 | Zhang et al. | |
| 6,251,660 | B1 | * 6/2001 | Muir et al. | 435/287.2 |

OTHER PUBLICATIONS

Corless et al. Contamination and Sensitivity Issues with a real–time Universal 16S rRNA PCR. Journal of Clinical Microbiology, vol. 38, No. 5, pp. 1747–1752, May 2000.*

C.E. Corless, M. Guiver, R. Borrow, V. Edwards–Jones, E. B. Kaczmarski and A. J. Fox; "Contanimation and Sensitivity Issues with a Real–Time Universal 16S rRAN PCR", Journal of Clinical Microbiology, May 2000, pp1747–1752.

M. G. Bergeron, D. KE, C. Menard, F. J. Picard, M. Gagnon, M. Bernier, M. Ouellette, P. H. Roy, S. Marcoux and W. D. Fraser, "Rapid Detection of Group B Streptococci in Pregnant Women at Delivery", The New England Journal of Medicine, vol. 343, No. 3, Jul. 20, 2000, pp. 175–179.

K. Sen and D. M. Asher, "Multiplex PCR for Detection of Enterobacteriaceae in Blood," Transfusion, vol. 41, Nov. 2001, pp. 1356–1364.

Greisen et al., "PCR primers and probes for the 16S rRNA gene of most species of pathogenic bacteria, including bacteria found in cerebrospinal fluid", *Journal of Clinical Microbiology,* (Feb. 1994), pp. 335–351, vol. 32, No. 2.

Kostrikis et al., "Spectral genotyping of human alleles", *Science,* (Feb. 1998), pp. 1228–1229, vol. 279.

Lu et al., "Use of PCR with universal primers and restriction endonuclease digestions for detection and identification of common bacterial pathogens in cerebrospinal fluid", *Journal of Clinical Microbiology,* (Jun. 2000), pp. 2076–2080, vol. 38, No. 36.

Ludwig, W. "B. japonicum 16s rRNA gene," Database GenBank, Accession No. X87272, (Jan. 1996).

Yanagi, et al. "Bradyrhizobium japonicum 16s rRNA gene," Database GenBank, Accession No. D12781, (Feb. 1999).

* cited by examiner

*Primary Examiner*—Kenneth R. Horlick
*Assistant Examiner*—Cynthia Wilder
(74) *Attorney, Agent, or Firm*—Banner & Witcoff, Ltd.

(57) ABSTRACT

An adaptation of the real-time PCR assay allows for highly sensitive detection of any eubacterial species with simultaneous speciation. The assay relies on a 'multiprobe' design in which a single set of highly conserved sequences encoded by the 16S rRNA gene serves as the primer pair, and it is used in combination with both an internal highly conserved sequence, the universal probe, and an internal variable region, the species-specific probe. A pre-PCR ultrafiltration step can be used to effectively decontaminate or remove background DNA. The real-time system reliably identifies 14 common bacterial species with a detection limit of 50 fg.

10 Claims, 5 Drawing Sheets

QUANTITATIVE ASSAY FOR THE SIMULTANEOUS DETECTION AND SPECIATION OF BACTERIAL INFECTIONS

This application claims priority to and incorporates by reference co-pending provisional application Ser. No. 60/272,642 filed Mar. 1, 2001, the disclosure of which is expressly incorporated herein.

The invention was made under funding from National Institutes of Health grant 3M01RR00052-39-5(S1). The U.S. government therefore retains certain rights in this invention.

FIELD OF THE INVENTION

The invention relates to the filed of clinical diagnoses. In particular it relates to diagnoses of bacterial infections generically and specifically.

BACKGROUND OF THE INVENTION

Currently, the standard method for diagnosing the presence of bacterial pathogens in clinical samples relies on culture techniques. However, active research is underway using new molecular methods to decrease detection time and increase assay sensitivity. Polymerase chain reaction (PCR) has emerged as the molecular method of choice in achieving these objectives. The utility of PCR and other molecular methods is evidenced by the recent guidelines issued by the 1999 National Committee for Clinical Laboratory Standards, encouraging the use of such methods in clinical laboratories performing bacterial identification assays (11).

To detect the presence of any bacterial pathogen in a clinical sample, primers annealing to regions of DNA conserved across a wide range of bacterial genomes have been employed. The design of such universal primers has often focused on the 16S rRNA gene (14). The presence of multiple copies of this gene within the bacterial genome facilitates its amplification by PCR. Further, sufficient sequence variability allows phylogenetic information to be attained for the purposes of microbial identification. However, up to the present, assays that provide for both universal detection and speciation require a second post-PCR processing step, which can be technically cumbersome and lengthen the time to reporting of results.

Contamination has plagued universal PCR-based bacterial detection systems. High sequence conservation of the DNA region chosen for PCR primer annealing coupled with the immense amplification power of PCR, results in the amplification of exceedingly minor bacterial contamination leading to false positives. Attempts to decontaminate PCR materials have involved nearly all known methods to destroy DNA including UV irradiation, 8-MOP treatment, and incubation with various enzymes such as DNase, restriction enzymes, or both in combination (2,3). Thus far, none of these methods have been shown to be entirely effective or reproducible.

Assessment of bacterial contamination can most reliably be made using real-time detection methods to characterize PCR amplification. Briefly, real-time PCR amplifications are reported by the cycle number at which PCR product accumulates significantly over baseline, as detected by interaction with fluorogenic probes ($C_T$) (7). Aside from saving time and labor, this technique has been shown to be more objective and consistent than the traditional methods of amplification detection and template quantification involving gel electrophoresis (13). With this more precise technique however, Corless et al. found that most decontamination methods decreased PCR sensitivity. The implication of this finding was that the decontamination effect of the aforementioned methodologies could at least in part be explained by a reduction of the sensitivity of the PCR amplification system.

The quantitative capacity of real-time PCR has thus redefined the standards by which a decontamination method is measured. Not only would a particular method be required to yield negative results for controls under the more precise probe-based real-time system, but also, the method must be shown to preserve the sensitivity of the PCR assay. There is a continuing need in the art for methods which preserve sensitivity and eliminate false positive results in detecting bacterial infections.

BRIEF SUMMARY OF THE INVENTION

One embodiment of the invention provides a method for detecting and determining species source of eubacterial DNA in a sample. Template DNA in a sample is amplified using a real-time polymerase chain reaction (PCR). The PCR employs primers and at least two fluorogenic probes. The primers amplify a segment of a *S. aureus* 16S rRNA gene comprising a conserved region and a first divergent region if a *S. aureus* 16 rRNA gene is present in a PCR reaction. The conserved region comprises at least 18 contiguous nucleotides which are at least 80% identical among at least 10 eubacterial species. The first divergent region comprises at least 10 contiguous nucleotides and differs by at least 3 nucleotides from a second divergent region found in *Bradyrhizobium japonicum* 16S rRNA gene. Each of the fluorogenic probes comprises a reporter dye and a quencher dye. A first of the two fluorogenic probes hybridizes to the conserved region and the second of the two fluorogenic probes hybridizes to a third divergent region of a first species of eubacteria. The reporter dyes of the first and the second probes have non-overlapping emission spectra. Fluorescence emissions of the reporter dyes are monitored. Presence of eubacteria in the sample is determined if emissions characteristic of the reporter dye of the first probe are detected. Presence of the first species of eubacteria in the sample is determined if emissions characteristic of the reporter dye on the second probe are detected.

Another embodiment of the invention provides another method for detecting and determining species source of eubacterial DNA in a sample. A real-time PCR reaction mixture is filtered to remove double stranded DNA contaminants having a length of ≧125 bp, forming a filtrate. The PCR reaction mixture comprises primers and at least two fluorogenic probes. The primers amplify a segment of a *S. aureus* 16S rRNA gene comprising a conserved region and a first divergent region if a *S. aureus* 16 rRNA gene is present in a PCR reaction. The conserved region comprises at least 18 contiguous nucleotides which are at least 80% identical among at least 10 eubacterial species. The first divergent region comprises at least 10 contiguous nucleotides and differs by at least 3 nucleotides from a second divergent region of *Bradyrhizobium japonicum* 16S rRNA gene. Each of the probes comprises a reporter dye and a quencher dye. A first of the two fluorogenic probes hybridizes to the conserved region and the second of the two fluorogenic probes hybridizes to a third divergent region of a first eubacterial species. The reporter dyes of the first and the second probes have non-overlapping emission spectra. A sample comprising template DNA is added to the filtrate. Template DNA in the filtrate is amplified. Fluorescence emissions of the reporter dyes are monitored. Presence of eubacteria in the sample is determined if emissions characteristic of the reporter dye of the first probe are detected. Presence of the first species of eubacteria in the sample is determined if emissions characteristic of the reporter dye on the second probe are detected.

Another aspect of the invention is a pair of polymerase chain reaction primers for amplifying a segment of a 16S rRNA gene of eubacteria comprising a conserved region and a divergent region. The pair comprises primers p890F and p1033R (SEQ ID NO: 1 and 2, respectively.)

A further embodiment of the invention is a kit for detecting bacteremia. One component of the kit is a pair of primers that amplify a segment of a *S. aureus* 16S rRNA gene if a *S. aureus* 16 rRNA gene is present in a PCR reaction. The segment comprises a conserved region and a first divergent region. The conserved region is common to at least 10 species of eubacteria. The first divergent region comprises at least 10 contiguous nucleotides and differs by at least 3 nucleotides from a second divergent region of 16S rRNA gene from *Bradyrhizobium japonicum*. Another component of the kit is at least two fluorogenic probes. Each probe comprises a reporter dye and a quencher dye. A first of the two fluorogenic probes hybridizes to the conserved region. A second of the two fluorogenic probes hybridizes to a third divergent region in a first species of eubacteria. The third divergent region comprises at least 10 contiguous nucleotides and differs by at least 3 nucleotides from the second divergent region. The reporter dyes of the first and the second probes have non-overlapping emission spectra.

The present invention thus provides the art with methods and tools for rapidly determining both the presence of bacteria in a sample and the type of bacteria present in a single reaction.

With pre-filtration (triangle), the detection limit was extended to 50 fg.

Figure 3:
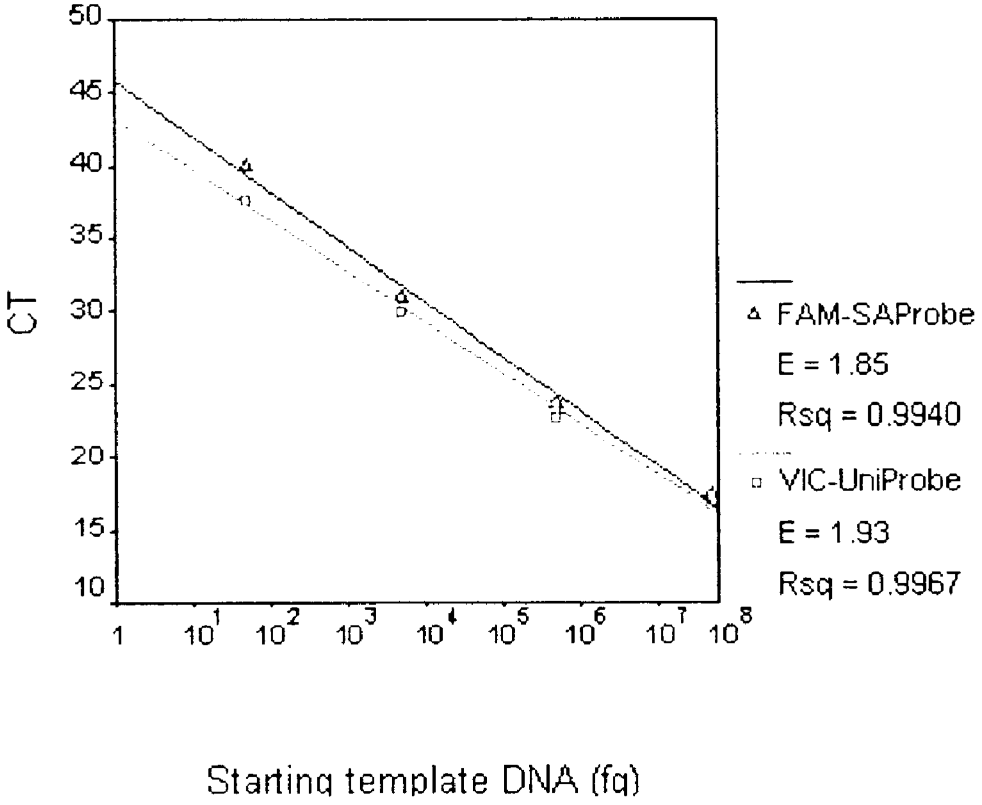

FIG. 3. Comparison of the standard curves for *S. aureus* DNA using universal probe (UniProbe) versus *S. aureus*-specific probe (SAProbe). PCR reactions generating the CT 's for the curves contained both UniProbe and SAProbe as well as *S. aureus* starting template DNA, which was serially diluted 1:100 from 50 ng to 50 fg. That the lines corresponding to UniProbe (square) and SAProbe (triangle) nearly overlay one another indicates comparable amplification efficiencies and detection limits for the different probes used in the same reaction mixtures. FAM and VIC refer to reporter dyes.

Figure 4:
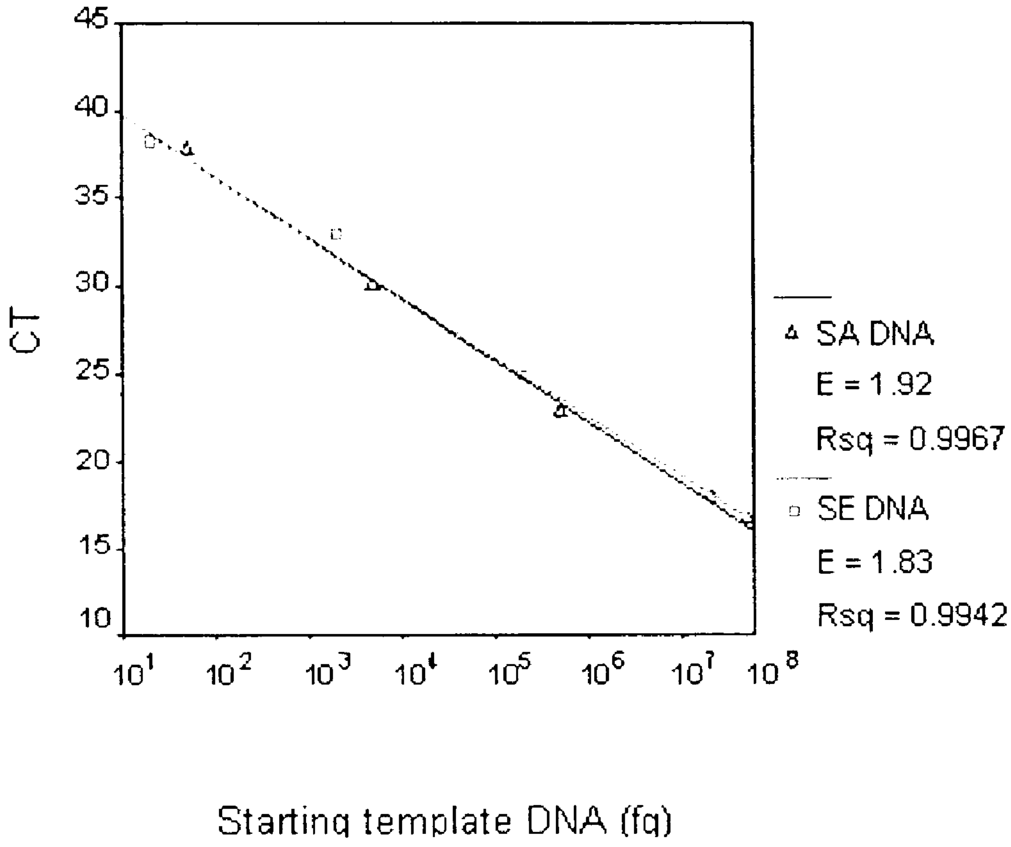

FIG. 4. Comparison of the standard curves for *S. aureus* versus *S. epidermidis* DNA using universal probe (UniProbe). PCR reactions generating the $C_T$'s for the curves contained UniProbe and either *S. aureus* or *S. epidermidis* starting template DNA. *S. aureus* DNA was serially diluted 1:100 from 50 ng to 50 fg whereas *S. epidermidis* DNA was diluted from 20 ng to 20 fg. The near equivalency of the lines indicates that UniProbe has equal detection capacity irrespective of whether *S. aureus* DNA (triangle) or *S. epidermidis* DNA (square) is used as starting template.

Figure 5:
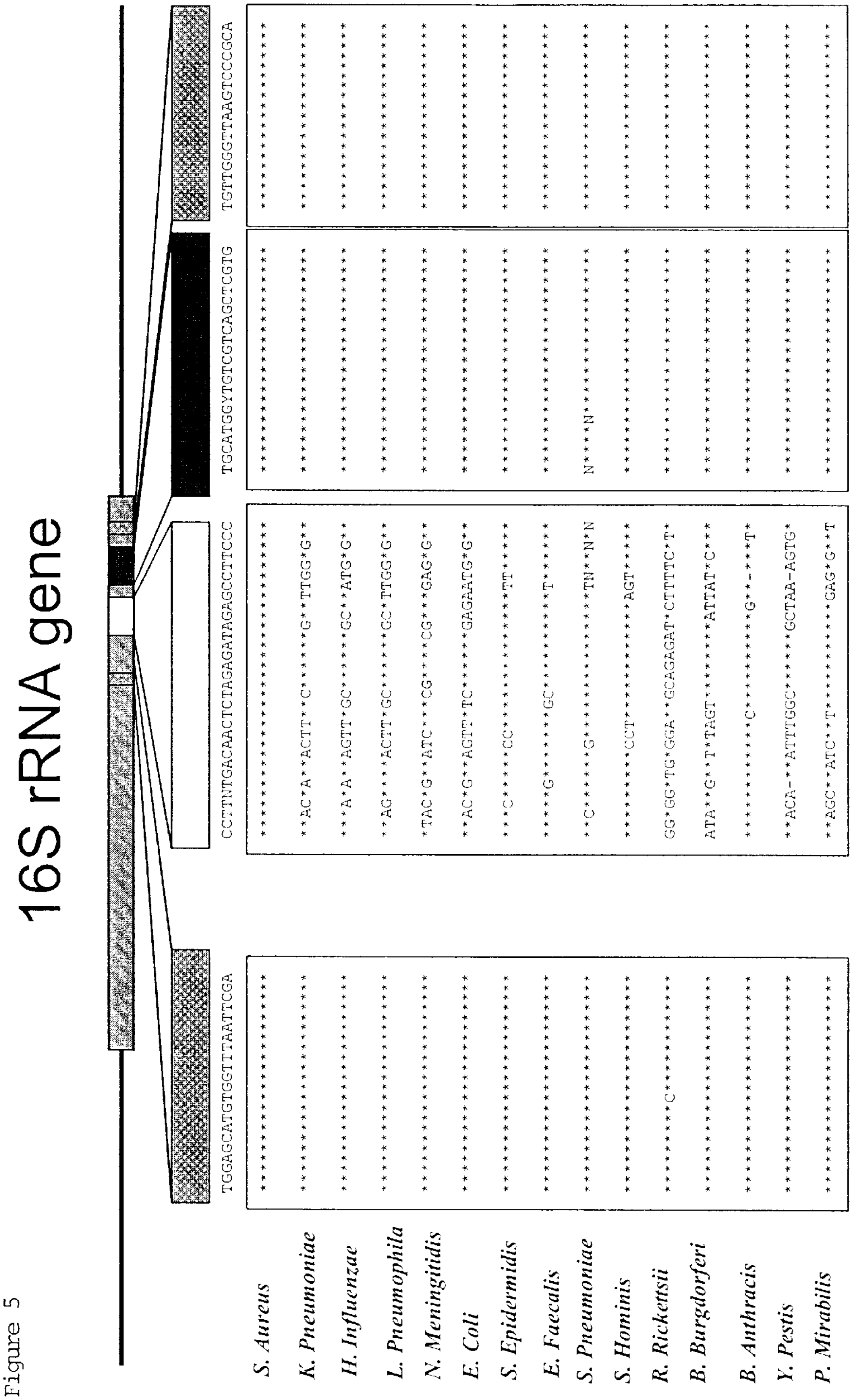

FIG. 5. Design of primers and probes for TaqMan PCR assay. The primer and probe sequences shown are as follows: TGGAGCATGTGGTTTAATTCGA (SEQ ID NO: 5); CCTTNTGACAACTCTAGAGATAGAGCCTTCCC (SEQ ID NO: 6); TGCATGGYTGTCGTCAGCTCGTG (SEQ ID NO: 7); TGTTGGGTTAAGTCCCGCA (SEQ ID NO: 8); TGGAGCATGCGGTTTAATTCGA (SEQ ID NO: 9); CCACNAGAACTTTCCAGAGATGGATTGGTGCC (SEQ ID NO: 10); CCTANAGAAGTTTGCAGAGATGCAGATGTGCC (SEQ ID NO: 11); CCAGNTGAACTTTGCAGAGATGCATTGGTGCC (SEQ ID NO: 12); CTACNGGAATCCTCCGGAGACGGAGGAGTGCC (SEQ ID NO: 13); CCACNGGAAGTTTTCAGAGATGAGAATGTGCC (SEQ ID NO: 14); CCTCNTGACCCCTCTAGAGATAGAGTTTTCCC (SEQ ID NO: 15); CCTTNGGACAACTGCAGAGATAGAGTCTTCCC (SEQ ID NO: 16); CCCTNTGACGACTCTAGAGATAGAGTNTTNCN (SEQ ID NO: 17); CCTTNTGACCCTTCTAGAGATAGAAGTTTCCC (SEQ ID NO: 18); GGTGGTTGCGGATCGCAGAGATGCTTTTCCTC (SEQ ID NO: 19); ATATNGGATATAGTTAGAGATAATTATTCCCC (SEQ ID NO: 20); CCTTNTGACAACCCTAGAGATAGGGCTTCTC (SEQ ID NO: 21); CCACAGAATTTGGCAGAGATGCTAAAGTGC (SEQ ID NO: 22); CCAGCTGATCACTCTAGAGATAGAGAGTGCCT (SEQ ID NO: 23); NGCATNGYTGTCGTCAGCTCGTG (SEQ ID NO: 24).

DETAILED DESCRIPTION OF THE INVENTION

We have devised a multiprobe-based, real-time PCR system involving the 16S rRNA gene, which allows for simultaneous detection of the presence of eubacterial DNA and discrimination of its species source. In addition, we devised a decontamination step for the current PCR system that reduces background contamination and does not compromise detection sensitivity.

The system is based on the use of PCR primers that prime virtually universally across species of eubacterial 16S rRNA genes. The amplicon that the primers amplify contains both a conserved region and a divergent region. Detection of the conserved region permits detection of eubacteria generically. Detection of a particular divergent region permits identification of a particular species of eubacteria. See FIG. 5.

Real-time polymerase chain reaction (PCR) is employed for the assay. This assay is known in the art and can be practiced generally according to the known methods. See for example, reference 8. Briefly, fluorogenic probes bind to template molecules and are degraded upon amplification of the template by the DNA polymerase. Degradation of the probes causes an increase in fluorescence that is monitored over time. The kinetics of fluorescence increase indicates the amount of template present in the reaction mixture.

Primers used in the present assays are able to amplify a segment of a *S. aureus* 16S rRNA gene that comprises both a conserved region and a first divergent region if a *S. aureus* 16 rRNA gene is present in a PCR reaction. The primers are virtually universal in applicability across the eubacteria.

Thus the primers amplify a segment of 16S rRNA genes of other eubacteria that also has the structure of containing both a highly conserved region and a divergent region. Thus the primers employed will amplify a segment of *S. aureus* 16S rRNA in the presence of *S. aureus* DNA template.

But they will amplify virtually any other eubacterial 16S rRNA in the presence of that eubacterial DNA template. Exemplary primers are shown in FIG. 5. Other primers having similar functional properties can also be used. These can be readily determined by inspection of known sequences of 16S rRNA genes or by use of computer programs such as ClustalW from the European Bioinformatics Institute http://ebi.ac.uk/clustalw.htm.

Conserved regions of 16S rRNA genes comprise at least 18 contiguous nucleotides that are at least 80% identical among at least 10 or at least 14 eubacterial species. The conserved regions can be at least 15, 20, 25, or 30 contiguous nucleotides. Preferably the regions are identical across a broad range of eubacterial species. However, divergence of up to 5, 10, 15, or 20% can be accommodated. The divergent regions comprise at least 10 contiguous nucleotides and differ by at least 3, 4, 5, or 6 nucleotides from a divergent region found in *Bradyrhizobium japonicum* 16S rRNA gene. See GenBank Accession Nos. D12781, X87272, and X71840. The divergent regions can comprises between 10 and about 30 contiguous nucleotides, and may be at least 15, 20, or 25 contiguous nucleotides.

Fluorogenic probes comprise a reporter dye and a quencher dye. In each assay of the invention one probe is used to hybridize to a conserved region and at least one probe is used to hybridize to a divergent region of eubacteria. If any eubacteria are present, regardless of species, hybridization to the conserved region will occur. However, hybridization may not occur to a divergent probe if the probe does not correspond to the species of eubacteria which is present. Multiple divergent probes may be used simultaneously in a single or multiple real-time PCR reactions to identify a particular species. Hybridization as used according to the present invention, refers to hybridization under standard conditions used for real-time PCR to achieve amplification.

Dyes on the probes that are used in a single reaction preferably have non-overlapping emission spectra. Thus their signals can be interpreted unambiguously as representing hybridization and/or amplification of a particular probe without further testing.

The primers of the present invention are defined in terms of their relationship to *S. aureus* 16S rRNA. However, as discussed above, other primers having similar properties can be used. The preferred amplicon which contains both a conserved and a divergent region bracketed by two conserved regions for primer binding preferably contains at least 100, 125, 150, 160, or 170 bp. A larger amplicon permits identification of more divergent regions which can be used to uniquely identify eubacterial species. A suitable segment of *S. aureus* 16S rRNA gene comprises nucleotides 890 to 1051. A conserved region of *S. aureus* 16S rRNA gene within this segment that can be utilized advantageously comprises nucleotides 1002 to 1024 of *S. aureus* 16S rRNA gene. A divergent region within this segment that can be utilized to identify *S. aureus* comprises nucleotides 945 to 978 of *S. aureus* 16S rRNA gene. Particularly preferred primers are p890F and p1033R (SEQ ID NO: 1 and 2, respectively.)

Samples to be tested are preferably clinical samples which are easy to obtain and easy to store. Suitable samples include without limitation blood, urine, saliva, tears, sweat, cerebrospinal fluid, lymph fluid, serum, and plasma. Samples can be treated as is known in the art to liberate DNA from cells in the samples. Particularly suitable samples are those from patients who are suspected due to clinical findings of having bacteremia.

One method for removing bacterial DNA that may be undesired contaminants of reagents or vessels is to use a filtration step. Preferably the filtration of the reagents will remove double-stranded DNA contaminants having a length of ≧125 bp. An alternative decontamination step can employ restriction endonuclease digestion of unwanted contaminating DNA. Care must be taken to ensure that the primers and probes are not susceptible to digestion by the restriction endonuclease employed. Preferably a site for digestion will be found within the amplicon but not within the primers themselves. Thus all components of the reaction mixture, excluding the test sample, can be treated with the restriction endonuclease. The restriction endonuclease is subsequently inactivated to prevent destruction of analyte in the test sample.

Kits may contain all or some of the reagents which will make practicing the invention practical. The reagents may be in single or divided containers. The reagents may be lyophilized or in solution or suspension, for example. Primers are desirably included as are probes for a conserved region and for one or more divergent regions of one or more eubacteria. Other reagents such as enzymes and nucleotides can also be included. Filters for decontamination of reagents can be provided as well. Written instructions for carrying out the methods can be included as well. These can take the form of package inserts or labels, or referrals to other sources such as books, journals, websites, compact discs, etc.

All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Materials and Methods

Bacterial Species and DNA Isolation

Fifteen common pathogenic microorganisms, all of which were eubacterial except one, *Candida albicans*, were obtained from the clinical laboratory (Division of Medical Microbiology, Johns Hopkins School of Medicine, Baltimore, Md.). The species and their ATCC strain are listed in Table 1. Microorganisms were grown in standard cultures, and DNA extracted using the QIAamp DNA kit (Qiagen Corp., Santa Clarita, Calif.).

With regard to generating standard curves for starting DNA template quantification, *Staphylococcus aureus* was grown in Luria-Bertani (LB) broth at 37° C. with continuous shaking to an optical density at 600 nm of 0.6. Equal aliquots were then plated to determine colony-forming units (CFU) and subjected to DNA extraction with the QIAamp DNA kit. The isolated DNA was quantified based on optical density at 260 nm and then serially diluted. Analogous procedures were performed for *Staphylococcus epidermidis*.

TABLE 1

Oligonucleotide sequences of primers and probes used in the study.

| Oligonucleotides | Sequences (5'→3')[a] | Position[b] (bp) | Fluorophores | $T_m$[c](° C.) |
|---|---|---|---|---|
| Forward Primer (P890F) | TGGAGCATGTGGTTTAATTCGA (SEQ ID NO:1) | 890–912 | — | 59.1 |
| Reverse Primer (P1033R) | TGCGGGACTTAACCCAACA (SEQ ID NO:2) | 1033–1051 | — | 58.6 |
| Universal Probe (UniProbe) | CACGAGCTGACGACARCCATGCA (SEQ ID NO:3) | 1002–1024 | VIC, TAMRA | 67.3/69.3 |
| *Staph Aureus* Probe (SAProbe) | CCTTTGACAACTCTAGAGATAGAGCCTTCCC (SEQ ID NO:4) | 945–978 | PAM, TAMRA | 65.3 |

[a]Sequences used for alignment *Staphylococcus aureus* (AF015929), *Staphylococcus hominis* (AY030318), *Enterococcus faecalis* (AJ276460), *Staphylococcus epidermidis* (L37605), *Enterococcus faecalis* (AJ276460), *Streptococcus pneumoniae* (X58312), *Mycoplasma pneumoniae* (AF132741), *Escherichia coli* (AF233451), *Hemophilus influenzae*, (AF224306), *Listeria pneumoniae* (M59157), *Neisseria meningitides* (AF059671), *Rickettsia rickettsii* (U11021), *Borrelia burgdorferi* (AF091368), *Bacillus anthracis* (AF290552), *Yersinia pestis* (AF366383), *Proteus mirabilis* (AF008582), and *K. pneumoniae* (AF228919)
[b]Nulceotide position based on *Staphylococcus aureus* sequences (AF015929)
[c]$T_m$, melting temperature.

Design of Primers and Probes

Figure 1:
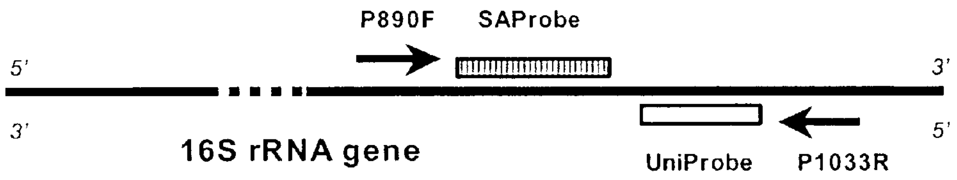
FIG. 1: Design of primers and probes. The forward (P890F) and reverse (P1033R) primers anneal to highly conserved regions of the 16S rRNA gene. An internal highly conserved region was selected as the annealing site of the universal Taqman probe (UniProbe), and the other internal region of highly variable sequence was selected as the annealing sites of a prototype species-specific probe for *S. aureus* (SAProbe).

The 16S rRNA gene sequences from a variety of bacterial species were obtained from GenBank. Sequence data were obtained using the program Entrez (see list below). The sequences were aligned using the program ClustalW from the European Bioinformatics Institute http://ebi.ac.uk/clustalw.htm. Two regions of highly conserved sequences, separated by both an internal region of highly variable sequence as well as another adjacent internal region of highly conserved sequence, were selected as the universal primer annealing sites. The internal highly conserved and highly variable sequences were used as the annealing sites of conserved and species-specific Taqman probes, respectively (FIG. 1).

The primers and Taqman probes were designed according to the guidelines in the ABI Primer Express software program (PE Applied Biosystems, Foster City, Calif.). This program selects probes and primer sets with optimized melting temperatures, secondary structure, base composition, and amplicon lengths. The forward primer (p890F) and reverse primer (p1033R) amplify a fragment of 162 bp spanning nucleotides 890 to 1051 of the *S. aureus* 16S rRNA gene (Table 1). The universal Taqman probe, or UniProbe, was labeled with the reporter dye VIC at the 5' end and the quencher dye TAMRA at the 3' end, and has the sequence which is the reverse complement of nucleotides 1002 to 1024 of the 16S rRNA gene (GenBank Accession no. AF015929) (Table 1). A *S. aureus*-specific probe, or SAProbe, was designed as the species-specific probe. The SAProbe was labeled with a different reporter dye, FAM, at the 5' end and the same quencher dye at the 3' prime end, with the sequence which spans nucleotides 945 to 978 of the *S. aureus* 16S rRNA gene (GenBank Accession no. AF015929) (Table 1). The probes were designed to anneal to opposite strands of the template DNA. The primers and probes were manufactured by PE Applied Biosystems.

PCR Master Mix and Fluorogenic-Probe Based PCR (TaqMan Assay)

Reactions were performed in 50 $\mu$l volumes in 0.5-ml optical-grade PCR tubes (PE-Applied Biosystems). PCR master mix was prepared from the Taqman Core Reagent Kit (PE-Applied Biosystems). The master mix was comprised of 200 $\mu$M (each) of dATP, dGTP, dUTP, dCTP, 0.5 U of AmpErase UNG, 2.5 mM $MgCl_2$, 1X Taqman Buffer A, 900 nM of each primer, and 100 nM of each fluorescent labeled probe (UniProbe and/or SAProbe). Template DNA, 2 U of AmpliTaq Gold DNA Polymerase (PE-Applied Biosystems), and water were added to give a final volume of 50 $\mu$l for each sample. The fluorogenic-probe based PCR, or Taqman assay, was performed using the ABI 7700 Sequence Detection system (PE-Applied Biosystems). The cycling conditions used were as follows: 50° C. for 2 min, 95° C. for 10 min, followed by 40 cycles at 95° C. for 15 seconds and 60° C. for 1 min each. All PCR reactions were performed in triplicate.

The correct size of the PCR product from each assay was verified by running an amplified sample from each reaction tube on agarose gels stained with ethidium bromide.

Ultrafiltration of the PCR Reaction Mix

An ultrafiltration step, using the Amicon Microcon YM-100 centrifugal filter device (Millipore Corporation, Bedford, Mass.) was utilized for filtering the PCR reaction mix prior to addition of template DNA. The PCR reaction mix that underwent ultrafiltration included the PCR master mix and AmpliTaq Gold DNA Polymerase.

This filtration device prevents the passage of potential contaminating double stranded DNA of 125 base pairs or greater. The PCR reaction mix was spun at 100× g for 30 minutes for decontamination purposes.

Post-PCR Analysis

Amplification data were analyzed by the SDS software (PE-Applied Biosystems), which calculates $\Delta R_n$ using the equation $R_n(+)-R_n(-)$. $R_n(+)$ is the emission intensity of the reporter divided by the emission intensity of the quencher at any given time, whereas $R_n(-)$ is the value of $R_n(+)$ prior to PCR amplification. Thus, $\Delta R_n$ indicates the magnitude of the signal generated. The threshold cycle, or $C_T$, is the cycle at which a statistically significant increase in $\Delta R_n$ is first detected. The $C_T$ is inversely proportional to the starting amount of target DNA. Amplification plots were generated with $\Delta R_n$ vs $C_T$ (5, 15).

Nucleotide Sequence Accession Numbers

The GenBank accession numbers for the sequences determined in this study are *Staphylococcus aureus* (AF015929), *Staphylococcus hominis* (AY030318), *Enterococcus faecalis* (AJ276460), *Staphylococcus epidermidis* (L37605), *Enterococcus faecalis* (AJ276460), *Streptococcus pneumoniae* (X58312), *Mycoplasma pneumoniae* (AF132741), *Escherichia coli* (AF233451), *Hemophilus influenzae*, (AF224306), *Legionella pneumophila* (M59157), *Neisseria meningitides* (AF059671), *Rickettsia rickettsii* (U11021), *Borrelia burgdorferi* (AF091368), *Bacillus anthracis* (AF290552), *Yersinia pestis* (AF366383), *Proteus mirabilis* (AF008582), and *Klebsiella pneumoniae* (AF228919).

Restriction Endonuclease Digestion

The restriction endonuclease, MboII, was selected for use in the pretreatment of the PCR master mixture on the basis of the unique location of its restriction site within the amplified region of the 16S RNA by use of the Sequencher software program (Gene Codes Corp). The MboII enzyme was chosen because it has a recognition site (5'-GAAGA $(N)_8^{v}$-3' within the amplified region of 16S rRNA which is highly conserved across species, and it has no digestion site within the probe or primer sequences. The ability of the enzyme to digest a false-positive product was demonstrated by incubating 0.20 1 $\mu l$ of MboII with 20 $\mu l$ of product at a37C for 1 hr, followed by heat inactivation of the restriction enzyme at 60° C. for 90 minutes and analysis by gel electrophoresis. For pretreatment of PCR reagents, 0.20 $\mu l$ of MboII was incubated with PCR master mix and DEPC water at 37° C. for 1 hr, followed by 60° C. for 90 minutes, before the addition of Low-DNA AmpliTaq DNA polymerase (PE-ABI) and template DNA.

EXAMPLE 2

Specificity of Universal TaqMan PCR

The specificity of the primers and probes used for universal amplification of eubacterial 16S rRNA gene was first assessed with genomic DNA extracts from 14 different bacterial species together with one isolate from *Candida albicans* (Table 2). In each PCR assay, 5 ng of purified DNA were used. The assay's positivity was determined by examination of the amplification plot ($C_T$ vs $\Delta R_n$) generated by the Sequence Detection Software (FIG. 1). All 14 bacterial species were correctly amplified and detected with $C_T$ values in the range of 19.2 to 21.8. No amplification ($C_T$>40) was detected when DNA isolated from *C. albicans* was used. The assay results were further verified by subjecting reaction products to gel electrophoresis, with visualization of bands of the expected size (162 bp) (data not shown).

TABLE 2

Specificity of the Taqman assay using universal primers and probes.

| Isolated Microorganisms | Strain (ATCC) | Taqman PCR results |
|---|---|---|
| *Staphylococcus aureus* | 29213 | + |
| *Staphylococcus hominis* | Clinical isolate | + |
| *Staphylococcus epidermidis* | Clinical isolate | + |
| *Streptococcus agalactiae* | Clinical isolate | + |
| *Streptococcus pneumoniae* | 49619 | + |
| *Klebsiella pneumoniae* | 990603 | + |
| *Listeria monocytogenes* | Clinical isolate | + |
| *Enterococcus faecalis* | 29212 | + |
| *Escherichia coli* | 25922 | + |
| *Proteus mirabilis* | 25933 | + |
| *Chlamydia pneumoniae* | Clinical isolate | + |
| *Neisseria gonorrhoeae* | Clinical isolate | + |
| *Neisseria meningitidis* | Clinical isolate | + |
| *Haemophilus influenzae* (Type A) | 49247 | + |
| *Candida albicans* | Clinical isolate | – |

EXAMPLE 3

Theoretical Detection Limit of TaqMan PCR

Figure 2:
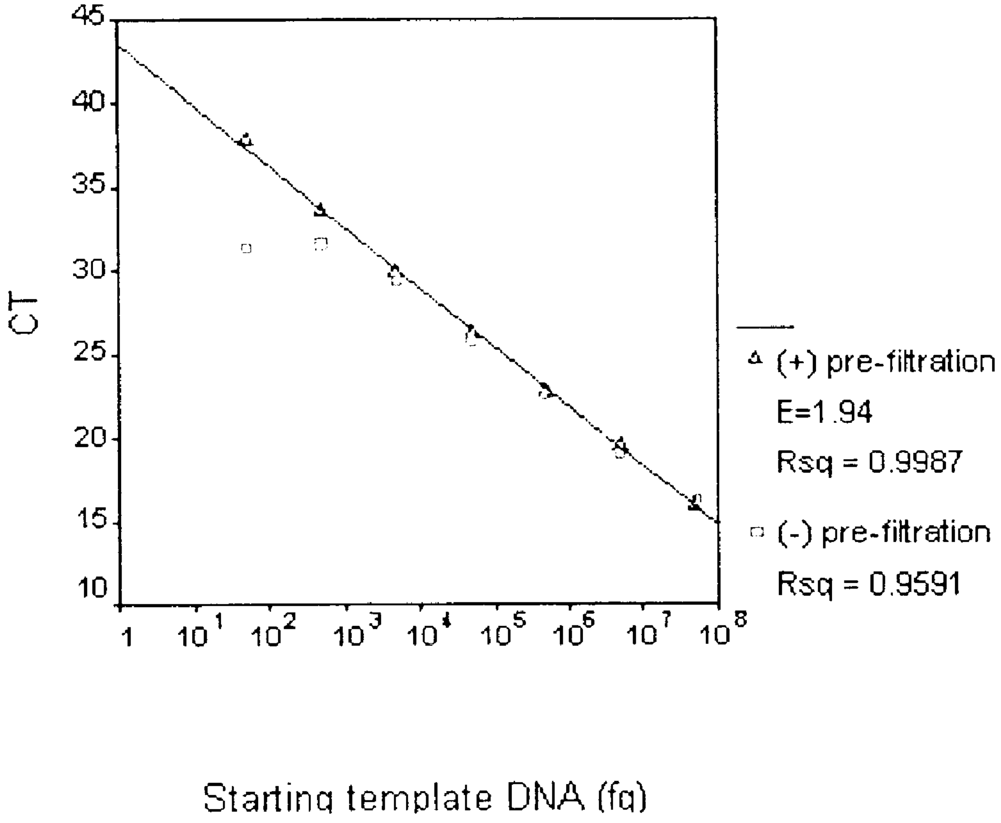
FIG. 2. Inverse linear relationship of $C_T$ versus starting template DNA with and without pre-filtration. $C_T$'s were generated from PCR reactions with starting template *S. aureus* DNA serially diluted 1:10 from 50 ng to 5 fg. In the non-pre-filtration curve (square), non-linearity is encountered at starting template DNA quantities below 5 pg, suggesting background eubacterial DNA contamination of this amount.

The sensitivity of the TaqMan assay was determined by amplifying serial dilutions of eubacterial DNA. The minimal detection limit of the TaqMan system was defined as the amount of template DNA at which the relationship between $C_T$ and starting template DNA became nonlinear. Serial dilutions of *S. aureus* DNA (50 ng to 5 fg) were added to PCR reactions with universal primers (p890F+p1033R) and probe (UniProbe). The results are shown in Table 3. The standard curve in which $C_T$ values were plotted against starting template DNA is linear between 50 ng to 5 pg (FIG. 2). At DNA levels below 5 pg, this relationship became non-linear, and the CT's were similar to the $C_T$ of the no template control (NTC). This suggested the presence of contaminating eubacterial DNA in the NTC. The minimal detection limit of the assay was thus 5 pg of *S. aureus* DNA.

TABLE 3

Sensitivity of the Taqman Assay with or without pre-filtration.

| | $C_T$ for the following template DNA concentration (~ equivalent cfu)* | | | | | | | | |
|---|---|---|---|---|---|---|---|---|---|
| Sample Type | NTC[a] | 50 ng ($10^7$) | 5 ng ($10^6$) | 500 pg ($10^5$) | 50 pg ($10^4$) | 5 pg ($10^3$) | 500 fg ($10^2$) | 50 fg (15) | 5 fg (1) |
| (–) filter | 31.5 | 16.2 | 19.1 | 22.5 | 25.8 | 29.5 | 31.6 | 31.3 | – |
| (+) filter | 40 | 16.8 | 19.6 | 22.8 | 26.2 | 30.0 | 33.7 | 37.8 | >40 |

*Mean values, based on triplicate samples
[a]No Template Control

As an effort to improve the detection limit of the assay, we implemented a pre-filtration step for the PCR reaction mix prior to the addition of template DNA, in addition to the conventional precautionary measures used for reducing contaminating or carry-over DNA present in PCR reagents. The filtration device retains contaminating DNA but allows for passage of all components of the PCR reaction mix, including primers, probes, Taq polymerase, and UNG. Addition of this pre-filtration step increased the $C_T$ of no template control to 40, effectively reducing the contaminating DNA (Table 3). $C_T$'s at DNA levels (50 ng to 5 pg) remained comparable with or without the pre-filtration step. Furthermore, the $C_T$ values of starting DNA template below 5 pg and those greater than 5 pg all fell on the same line with an $R^2$=0.998. (FIG. 2).

The efficiency (E) of the pre-filtered PCR amplification was calculated to be 1.94 (maximum =2) based on the equation:

$$\text{Efficiency}=e^{(-1/slope)}$$

The minimum detection limit of the assay with pre-filtration was 50 fg of *S. aureus* DNA (Table 3). Based on the size of the *S. aureus* genome, which is approximately 2,750 kbp, 50 fg of *S. aureus* DNA is equivalent to approximately 15 genomes or cfu. This was calculated as follows: 2750 kb is equal to $1.8\times10^6$ g/mol; dividing this value by Avogadro's number, $6\times10^{23}$, yields 3 fg per *S. aureus* genome. Comparable results were derived empirically based on counting cfu's on plates.

The amplified products were subsequently subjected to gel electrophoresis. Visualization of the bands under UV irradiation confirmed the expected amplicon size (data not shown).

EXAMPLE 4

Multi-Probe Assay.

In order to demonstrate the assay's ability to simultaneously detect the presence of any eubacterial DNA as well as one or more species of interest within a single reaction tube, a prototype species-specific probe for *S. aureus* (SAProbe) was designed. The SAProbe was labeled with a different reporter fluorophore so that its signal could be distinguished from that of the universal probe. Real-time PCR assays were performed with the universal primer set, UniProbe, and SAProbe in a single reaction mix. Template DNA samples from one of three closely related Staphylococcus species, *S. aureus, S. epidermidis, S. hominis* were tested in three different reactions. The assay correctly detected the presence of eubacterial DNA in all three samples under the VIC dye layer. When the detection system was re-configured to detect the FAM dye layer in the same reaction tubes, only the reaction containing *S. aureus* DNA yielded a positive signal (Table 4).

TABLE 4

Specificity of the multiprobing PCR.

| | NTC[a] | *S. aureus* | *S. epidermidis* | *S. hominis* |
|---|---|---|---|---|
| VIC-UniProbe | − | + | + | + |
| FAM-SAProbe | − | + | − | − |

[a]No Template Control

PCR results between reactions using UniProbe versus SAProbe showed no significant differences in $C_T$ values for amplifications with equivalent amounts of *S. aureus* DNA (Table 5). Detection equivalence is also described in FIG. 3 with standard curves in which $C_T$'s are plotted against starting template DNA. The similar slopes of the two lines indicates equal efficiencies; the coinciding extrapolated axis intercepts, equal detection limits.

TABLE 5

Comparison of multiprobing PCR results in single versus dual infection.

| | $C_T$ of the following sample types in multiprobe PCR* | | | | | | | | | | | |
|---|---|---|---|---|---|---|---|---|---|---|---|---|
| | *S. aureus*(SA) | | | | *S. epidermidis*(SE) | | | | 200 pg of SE + SA | | | |
| Probe | 50 ng | 500 pg | 5 pg | 50 fg | 20 ng | 200 pg | 2 pg | 20 fg | 50 ng | 500 pg | 5 pg | 50 fg |
| VIC-UniProbe | 16.8 | 22.8 | 30.0 | 37.8 | 18.1 | 24.8 | 32.9 | 38.2 | 16.6 | 22.8 | 24.1 | 25.0 |
| FAM-SAProbe | 17.4 | 23.7 | 31.1 | >40 | >40 | >40 | >40 | >40 | 17.2 | 23.1 | 32.0 | >40 |

*Mean values, based on triplicate samples

PCR results using UniProbe with serial dilutions of *S. epidermidis* template DNA yielded results similar to those with S. aureus template DNA. Specifically, plots of $C_T$'s against starting template DNA revealed almost equivalent amplification efficiencies between the two (FIG. 4). PCR results using SAProbe with serial dilutions of *S. epidermidis* template DNA gave no detection (Table 5).

Finally, PCR reactions using both probes with a constant amount of *S. epidermidis* template DNA and serial dilutions of *S. aureus* template DNA were performed. SAProbe results coincided with the titration in which only *S. aureus* DNA was serially diluted. UniProbe results differed however. At concentrations in which *S. aureus* DNA predominated over that of *S. epidermidis*, the $C_T$'s of the UniProbe results were comparable with those of the SAProbe. As the amount of *S. aureus* DNA was diluted and the *S. epidermidis* DNA became predominant, the $C_T$'s leveled off at a value corresponding to the constant amount of *S. epidermidis* DNA added to each reaction tube (Table 5).

EXAMPLE 5

Current methods of universal detection with speciation include PCR amplification with a universal primer set followed by performance of a species identification assay such as oligonucleotide array, restriction digestion, or sequencing (1,5,10). Another variation has been to culture clinical samples and subsequently subject the bacteria to different sets of probes (9). Regardless of the methodology, virtually all techniques for universal detection and speciation of bacteria have thus far involved at least two sequential steps.

With the probe-based PCR system described here, both steps can for the first time be accomplished simultaneously.

The probe-based PCR system we have devised is comprised of a universal primer set, a universal probe, and a species-specific probe. In this way, detection of amplification, and extraction of sequence information from amplicons can be performed within the confines of the PCR run, eliminating the need for post-PCR manipulations. This innovation reduces overall assay time to about two hours or less, depending on the PCR instrument used, while conserving the sensitivity and specificity of the assay.

The only current limitation of this system is inherent to the number of fluorophores commercially available and the discriminatory power of the detection instrument itself, which currently can simultaneously differentiate up to four different fluorophores in a single tube (14). Thus, the number of species-specific probes which may be included in an individual reaction (in addition to the universal probe) is restricted.

Simultaneous detection and/or speciation of microorganisms in a given sample has been reported recently using the multiplexing technique, with multiple sets of species-specific primer pairs and probes corresponding to different amplification targets (3). Our novel PCR design in which multiple probes, including a universally conserved one, exploit regions within the same amplification target does confer several advantages over multiplexing. First, possible competition between multiple PCR primer pairs is avoided with multiprobing, which involves only a single pair of primers. Moreover, when technologies advance to allow for more flourophores, expansion of the multiprobe system for detection of other templates will require only the addition of another probe. This is in contrast to multiplexing, in which both new primers and probes will have to be added to the reaction mixture. In that circumstance, the new primers may not amplify under the original PCR conditions, which would thus require optimization studies to accommodate all the primer pairs. Finally, even if suitable conditions were ultimately attained, amplification efficiencies may be altered such that standard curves for starting template quantification would need to be rederived. Since multiprobing involves only a single target region, quantification of starting template will in principle, rely on only one standard curve, if all probes are designed with a similar $T_m$.

With regard to contamination, residual bacterial DNA from various sources has historically prevented widespread use of universal primer sets in PCR-based assays. In our experience, pretreatment of PCR reagents with restriction enzymes followed by heat inactivation did eliminate amplification in the negative controls. However, $C_T$ values for positive controls from runs with pre-treated reagents were consistently greater than those without pretreatment (data not shown). Whether these findings reflected residual restriction enzyme activity even after heat inactivation, or systemic inhibition of the PCR system by the addition of restriction enzyme is unknown.

The contamination problem was eventually resolved by passing PCR reagents through Microcon YM-100 centrifugal filter devices (Millipore Corporation). Of note, these filters allow decontamination of all PCR reagents, including UNG, Taq polymerase, primers, and probes, which was not possible using other methods, such as DNAase treatment. Although Centricons have been employed for decontamination purposes in the past, heretofore, their adequacy in the context of real-time PCR systems had not been studied (16). With prefiltration, the PCR efficiency of the system was not reduced. In addition, with significant reduction in background contamination, the prefiltration step improved the minimum detection limit of the assay from 5000 fg to 50 fg of *S. aureus* DNA. The mean $C_T$ of the negative-control was 40. In our experience, the $C_T$ values of negative controls, although consistently above 35, were variable. These results were not unexpected since greater sampling errors are encountered at low starting template concentrations (12).

References

1. Anthony R M, Brown T J, French G L. 2000. Rapid diagnosis of bacteremia by universal amplification of 23S ribosomal DNA followed by hybridization to an oligonucleotide array. J Clin Microbiol 38:781–8.
2. Carroll N M, Adamson P, Okhravi N. 1999. Elimination of bacterial DNA from Taq DNA polymerases by restriction endonuclease digestion. J Clin Microbiol 37:3402–4.
3. Corless C E, Guiver M, Borrow R, Edwards-Jones V, Fox A J, Kaczmarski E B. 2001. Simultaneous Detection of *Neisseria meningitidis, Haemophilus influenzae*, and *Streptococcus pneumoniae* in Suspected Cases of Meningitis and Septicemia Using Real-Time PCR. J Clin Microbiol 39:1553–8.
4. Corless, C E, Guiver M, Borrow R, Edwards-Jones V, Kaczmarski E B, and Fox A J. 2000. Contamination and sensitivity issues with a real-time universal 16S rDNA PCR. J. Clin. Microbiol. 38:1747–1752
5. Gibson U E, Heid C A, and Williams P M. 1996. A novel method for real time quantitative RT-PCR. Genome Research 6:995–100
6. Goldenberger D, Kunzli A, Vogt P, Zbinden R, Altwegg M. 1997. Molecular diagnosis of bacterial endocarditis by broad-range PCR amplification and direct sequencing. J Clin Microbiol 35:2733–9.
7. Guiver M, Borrow R, Marsh J, Gray S J, Kaczmarski E B, Howells D, Boseley P, Fox A J. 2000. Evaluation of the Applied Biosystems automated Taqman polymerase chain reaction system for the detection of meningococcal DNA. FEMS Immunol Med Microbiol 28:173–9.
8. Heid C A, Stevens J, Livak K J, Williams P M. 1996. Real time quantitative PCR. Genome Res. 6:986–94.
9. Lu J J, Perng C L, Lee S Y, Wan C C. 2000. Use of PCR with universal primers and restriction endonuclease digestions for detection and identification of common bacterial pathogens in cerebrospinal fluid. J Clin Microbiol 38:2076–80.
10. McCabe K M, Zhang Y H, Huang B L, Wagar E A, McCabe E R. 1999. Bacterial species identification after DNA amplification with a universal primer pair. Mol Genet Metab 66:205–11.
11. National Committee for Clinical Laboratory Standards. 1999. Molecular diagnostic methods for infectious diseases. Approved guideline MM3-A. National Committee for Clinical Laboratory Standards, Wayne, Pa.
12. Rantakokko-Jalava K, Nikkari S, Jalava J, Eerola E, Skurnik M, Meurman O, Ruuskanen O, Alanen A, Kotilainen E, Toivanen P, Kotilainen P. 2000. Direct amplification of rDNA genes in diagnosis of bacterial infections. J Clin Microbiol 38:329.
13. Rassmussen, R. 2001. Quantification on the LightCycler. http://www.idahotech.com/lightcycler_u/lectures/quantifiaction_on_lc.htm.
14. Schmittgen T D, Zakrajsek B A, Mills A G, Gorn V, Singer M J, Reed M W 2000. Quantitative Reverse Transcription-Polymerase Chain Reaction to Study mRNA Decay: Comparison of Endpoint and Real-Time Methods. Analytical Biochemistry 285, 194–204.

15. Sen K.2000. Rapid Identification of *Yersinia enterocolitica in Blood by the* 5' Nuclease PCR Assay. Journal of Clinical Microbiology 38: 1953–1958

16. Vet J A, Majithia A R, Marras S A, Tyagi S, Dube S, Poiesz B J, and Kramer F R 1999. Multiplex detection of four pathogenic retroviruses using molecular beacons. Proc Natl Acad Sci U.S.A. 96: 6394–6399.

17. Wilson K H, Blitchington R B, Greene R C. 1990. Amplification of bacterial 16S ribosomal DNA with polymerase chain reaction. J Clin Microbiol 28:1942–6.

18. Wages J M Jr, Cai D, Fowler A K. 1994. Removal of contaminating DNA from PCR reagents by ultrafiltration. Biotechniques 16:1014–7.

What is claimed is:

1. A pair of polymerase chain reaction primers for amplifying a segment of a 16S rRNA gene of eubacteria comprising a conserved region and a divergent region, said pair comprising primers p890F and p1033R (SEQ ID NO: 1 and 2, respectively.)

2. A kit for detecting bacteremia, comprising:

a pair of primers that amplify a segment of a *S. aureus* 16S rRNA gene if in the presence of the gene, said segment comprising a conserved region and a first divergent region, wherein the conserved region is common to at least 10 species of eubacteria, wherein the first divergent region comprises at least 10 contiguous nucleotides and differs by at least 3 nucleotides from a second divergent region of 16S rRNA gene from *Bradyrhizobium japonicum*; and at least two fluorogenic probes, each probe comprising a reporter dye and a quencher dye, a first of the two fluorogenic probes hybridizing to the conserved region and a second of the two fluorogenic probes hybridizing to a third divergent region in a first species of eubacteria, wherein said third divergent region comprises at least 10 contiguous nucleotides and differs by at least 3 nucleotides from the second divergent region, wherein the reporter dyes of the first and the second probes have non-overlapping emission spectra.

3. The kit of claim 2 further comprising:

a third fluorogenic probe, wherein said third fluorogenic probe hybridizes to a fourth divergent region of 16S rRNA in a second species of eubacteria, wherein said fourth divergent region comprises at least 10 contiguous nucleotides and differs by at least 3 nucleotides from the second divergent region;

and wherein the reporter dye of the third fluorogenic probe has a non-overlapping emission spectrum from the dyes on the first and second probes.

4. The kit of claim 2 further comprising:

a fourth fluorogenic probe, wherein said fourth fluorogenic probe hybridizes to a fifth divergent region of 16S rRNA in a third species of eubacteria, wherein said fifth divergent region comprises at least 10 contiguous nucleotides and differs by at least 3 nucleotides from the second divergent region, and wherein the reporter dye of the fourth fluorogenic probe has a non-overlapping emission spectrum from the dyes of the first, second, and third probes.

5. The kit of claim 2 wherein the pair of primers are p890F and p 1033R (SEQ ID NO: 1 and 2, respectively.)

6. The kit of claim 2 wherein the conserved region comprises nucleotides 1002 to 1024 of *S. aureus* 16S rRNA gene.

7. The kit of claim 2 wherein the first divergent region comprises nucleotides 945 to 978 of *S. aureus* 16S rRNA gene.

8. The kit of claim 2 further comprising a filter for removing double stranded DNA >125 bp in length.

9. The kit of claim 2 further comprising written instructions for analyzing eubacterial infections using the primers and probes.

10. The kit of claim 2 further comprising reagents for carrying out real-time PCR.

* * * * *

UNITED STATES PATENT AND TRADEMARK OFFICE
Certificate

Patent No. 6,699,670 B2 | Patented: March 2, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Richard Eric Rothman, Cockeysville, MD (US); Samuel Yang, Baltimore, MD (US); Shin Lin, Baltimore, MD (US); Gabor David Kelen, Baltimore, MD (US); and Charlotte A. Gaydos, Bel Air, MD (US).

Signed and Sealed this Seventeenth Day of July 2007.

GARY BENZION
*Supervisory Patent Examiner*
Art Unit 1637

UNITED STATES PATENT AND TRADEMARK OFFICE

CERTIFICATE OF CORRECTION

PATENT NO. : 6,699,670 B2 Page 1 of 1
APPLICATION NO. : 10/085134
DATED : March 2, 2004
INVENTOR(S) : Richard Eric Rothman et al.

It is certified that error appears in the above-identified patent and that said Letters Patent is hereby corrected as shown below:

In Column 24, Claim 4, Line 6:
Please replace "claim 2" with --claim 3--

In Column 24, Claim 8, Line 25:
Please replace ">" with --≥--

Signed and Sealed this

Tenth Day of March, 2009

JOHN DOLL
*Acting Director of the United States Patent and Trademark Office*

SEQUENCE LISTING

<160> NUMBER OF SEQ ID NOS: 24

<210> SEQ ID NO 1
<211> LENGTH: 22
<212> TYPE: DNA
<213> ORGANISM: Staphylococcus aureus

<400> SEQUENCE: 1
tggagcatgt ggtttaattc ga 22

<210> SEQ ID NO 2
<211> LENGTH: 19
<212> TYPE: DNA
<213> ORGANISM: Staphylococcus aureus

<400> SEQUENCE: 2
tgcgggactt aacccaaca 19

<210> SEQ ID NO 3
<211> LENGTH: 23
<212> TYPE: DNA
<213> ORGANISM: Staphylococcus aureus

<400> SEQUENCE: 3
cacgagctga cgacarccat gca 23

<210> SEQ ID NO 4
<211> LENGTH: 31
<212> TYPE: DNA
<213> ORGANISM: Staphylococcus aureus

<400> SEQUENCE: 4
cctttgacaa ctctagagat agagccttcc c 31

<210> SEQ ID NO 5
<211> LENGTH: 22
<212> TYPE: DNA
<213> ORGANISM: Staphylococcus aureus

<400> SEQUENCE: 5
tggagcatgt ggtttaattc ga 22

<210> SEQ ID NO 6
<211> LENGTH: 32
<212> TYPE: DNA
<213> ORGANISM: Staphylococcus aureus
<220> FEATURE:
<221> NAME/KEY: misc_feature
<222> LOCATION: (1)..(32)
<223> OTHER INFORMATION: n = g, a, t, or c

<400> SEQUENCE: 6
ccttntgaca actctagaga tagagccttc cc 32

-continued

<210> SEQ ID NO 7
<211> LENGTH: 23
<212> TYPE: DNA
<213> ORGANISM: Staphylococcus aureus

<400> SEQUENCE: 7
tgcatggytg tcgtcagctc gtg 23

<210> SEQ ID NO 8
<211> LENGTH: 19
<212> TYPE: DNA
<213> ORGANISM: Staphylococcus aureus

<400> SEQUENCE: 8
tgttgggtta agtcccgca 19

<210> SEQ ID NO 9
<211> LENGTH: 22
<212> TYPE: DNA
<213> ORGANISM: Rickettsia rickettsii

<400> SEQUENCE: 9
tggagcatgc ggtttaattc ga 22

<210> SEQ ID NO 10
<211> LENGTH: 32
<212> TYPE: DNA
<213> ORGANISM: Klebsiella pneumoniae
<220> FEATURE:
<221> NAME/KEY: misc_feature
<222> LOCATION: (1)..(32)
<223> OTHER INFORMATION: n = g, a, t, or c

<400> SEQUENCE: 10
ccacnagaac tttccagaga tggattggtg cc 32

<210> SEQ ID NO 11
<211> LENGTH: 32
<212> TYPE: DNA
<213> ORGANISM: Haemophilus influenzae
<220> FEATURE:
<221> NAME/KEY: misc_feature
<222> LOCATION: (1)..(32)
<223> OTHER INFORMATION: n = g, a, t, or c

<400> SEQUENCE: 11
cctanagaag tttgcagaga tgcagatgtg cc 32

<210> SEQ ID NO 12
<211> LENGTH: 32
<212> TYPE: DNA
<213> ORGANISM: Legionella pneumophila
<220> FEATURE:
<221> NAME/KEY: misc_feature
<222> LOCATION: (1)..(32)
<223> OTHER INFORMATION: n = g, a, t, or c

<400> SEQUENCE: 12
ccagntgaac tttgcagaga tgcattggtg cc 32

<210> SEQ ID NO 13
<211> LENGTH: 32
<212> TYPE: DNA
<213> ORGANISM: Neisseria meningitidis
<220> FEATURE:
<221> NAME/KEY: misc_feature
<222> LOCATION: (1)..(32)

-continued

<223> OTHER INFORMATION: n = g, a, t, or c

<400> SEQUENCE: 13
ctacnggaat cctccggaga cggaggagtg cc 32

<210> SEQ ID NO 14
<211> LENGTH: 32
<212> TYPE: DNA
<213> ORGANISM: Escherichia coli
<220> FEATURE:
<221> NAME/KEY: misc_feature
<222> LOCATION: (1)..(32)
<223> OTHER INFORMATION: n = g, a, t, or c

<400> SEQUENCE: 14
ccacnggaag ttttcagaga tgagaatgtg cc 32

<210> SEQ ID NO 15
<211> LENGTH: 32
<212> TYPE: DNA
<213> ORGANISM: Staphylococcus epidermidis
<220> FEATURE:
<221> NAME/KEY: misc_feature
<222> LOCATION: (1)..(32)
<223> OTHER INFORMATION: n = g, a, t, or c

<400> SEQUENCE: 15
cctcntgacc cctctagaga tagagttttc cc 32

<210> SEQ ID NO 16
<211> LENGTH: 32
<212> TYPE: DNA
<213> ORGANISM: Enterococcus faecalis
<220> FEATURE:
<221> NAME/KEY: misc_feature
<222> LOCATION: (1)..(32)
<223> OTHER INFORMATION: n = g, a, t, or c

<400> SEQUENCE: 16
ccttnggaca actgcagaga tagagtcttc cc 32

<210> SEQ ID NO 17
<211> LENGTH: 32
<212> TYPE: DNA
<213> ORGANISM: Streptococcus pneumoniae
<220> FEATURE:
<221> NAME/KEY: misc_feature
<222> LOCATION: (1)..(32)
<223> OTHER INFORMATION: n = g, a, t, or c

<400> SEQUENCE: 17
ccctntgacg actctagaga tagagtnttn cn 32

<210> SEQ ID NO 18
<211> LENGTH: 32
<212> TYPE: DNA
<213> ORGANISM: Staphylococcus hominis
<220> FEATURE:
<221> NAME/KEY: misc_feature
<222> LOCATION: (1)..(32)
<223> OTHER INFORMATION: n = g, a, t, or c -continued

<400> SEQUENCE: 18
ccttntgacc cttctagaga tagaagtttc cc 32

<210> SEQ ID NO 19
<211> LENGTH: 32
<212> TYPE: DNA
<213> ORGANISM: Rickettsia rickettsii

<400> SEQUENCE: 19
ggtggttgcg gatcgcagag atgcttttcc tc 32

<210> SEQ ID NO 20
<211> LENGTH: 32
<212> TYPE: DNA
<213> ORGANISM: Borrelia burgdorferi
<220> FEATURE:
<221> NAME/KEY: misc_feature
<222> LOCATION: (1)..(32)
<223> OTHER INFORMATION: n = g, a, t, or c

<400> SEQUENCE: 20
atatnggata tagttagaga taattattcc cc 32

<210> SEQ ID NO 21
<211> LENGTH: 31
<212> TYPE: DNA
<213> ORGANISM: Bacillus anthracis
<220> FEATURE:
<221> NAME/KEY: misc_feature
<222> LOCATION: (1)..(31)
<223> OTHER INFORMATION: n = g, a, t, or c

<400> SEQUENCE: 21
ccttntgaca accctagaga tagggcttct c 31

<210> SEQ ID NO 22
<211> LENGTH: 30
<212> TYPE: DNA
<213> ORGANISM: Yersinia pestis

<400> SEQUENCE: 22
ccacagaatt tggcagagat gctaaagtgc 30

<210> SEQ ID NO 23
<211> LENGTH: 32
<212> TYPE: DNA
<213> ORGANISM: Proteus mirabilis

<400> SEQUENCE: 23
ccagctgatc actctagaga tagagagtgc ct 32

<210> SEQ ID NO 24
<211> LENGTH: 23
<212> TYPE: DNA
<213> ORGANISM: Streptococcus pneumoniae
<220> FEATURE:
<221> NAME/KEY: misc_feature
<222> LOCATION: (1)..(23)
<223> OTHER INFORMATION: n = g, a, t, or c

<400> SEQUENCE: 24
ngcatngytg tcgtcagctc gtg 23